(12) United States Patent
Hasegawa et al.

(10) Patent No.: US 6,800,185 B2
(45) Date of Patent: Oct. 5, 2004

(54) METHOD FOR PRODUCING BASIC AMINO ACID SOLUTION

(75) Inventors: Kazuhiro Hasegawa, Kawasaki (JP); Toshiya Tanabe, Kawasaki (JP); Yasuhiro Maruta, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 127 days.

(21) Appl. No.: 10/097,752

(22) Filed: Mar. 15, 2002

(65) Prior Publication Data

US 2002/0153261 A1 Oct. 24, 2002

(30) Foreign Application Priority Data

Mar. 23, 2001 (JP) .......................................... 2001-084456

(51) Int. Cl.[7] .............................................. B01D 61/44
(52) U.S. Cl. ........................ 204/530; 204/539; 204/541
(58) Field of Search ................................. 204/530, 539, 204/541, 531

(56) References Cited

U.S. PATENT DOCUMENTS

| | | | |
|---|---|---|---|
| 3,051,640 A | * 8/1962 | Traxler | 204/530 |
| 4,238,306 A | * 12/1980 | Perry et al. | 204/530 |
| 4,238,307 A | * 12/1980 | Perry et al. | 204/530 |
| 5,770,409 A | 6/1998 | Pfefferle et al. | |
| 6,133,000 A | 10/2000 | Pfefferle et al. | |
| 6,329,548 B1 | 12/2001 | Hasegawa et al. | |
| 6,551,803 B1 | * 4/2003 | Fischer et al. | 204/530 |

FOREIGN PATENT DOCUMENTS

| | | |
|---|---|---|
| EP | 0 532 867 A1 | 3/1993 |
| JP | 35-7666 | 6/1960 |
| JP | 50-30985 | 2/1993 |
| JP | 05-244969 | 9/1993 |
| JP | 2000-256292 | 9/2000 |

* cited by examiner

*Primary Examiner*—Arun S. Phasge
(74) *Attorney, Agent, or Firm*—Oblon, Spivak, McClelland, Maier & Neustadt, P.C.

(57) ABSTRACT

Herein are disclosed a method for producing a basic amino acid solution which comprises subjecting a solution of a basic amino acid salt to electrodialysis with the use of an electrodialyser equipped with cation exchange membranes and anion exchange membranes in combination, wherein an alkali aqueous solution is added to the solution of a basic amino acid salt during the electrodialysis, whereby not only desalting is caused but also the counter anions of the basic amino acid are removed to such degree that the said counter anions remain in an amount of 40 mol % or smaller based on the basic amino acid, as well as a method for producing a basic amino acid solution which comprises subjecting a solution of a basic amino acid salt to electrodialysis with the use of an electrodialyser equipped with anion exchange membrane alone, wherein an alkali aqueous solution is added to the solution of a basic amino acid salt to adjust the pH of the solution to 7 to 10 during the electrodialysis, whereby the counter anions are removed.

According to these methods, a basic amino acid solution having a high concentration within the concentration range in which crystals of a basic amino acid salt are not deposited, can be easily provided, by removing the counter anions from a solution of a basic amino acid salt efficiently by use of electrodialysis.

19 Claims, 1 Drawing Sheet

METHOD FOR PRODUCING BASIC AMINO ACID SOLUTION

BACKGROUND OF THE INVENTION

1. Technical Field of the Invention

The present invention relates to a method for producing a basic amino acid such as L-lysine known as an important additive for livestock feed or L-arginine or L-histidine useful as a drug such as an infusion solution (i.e., parenteral fluid) or the like.

2. Related Art

In a conventionally known method for producing a basic amino acid by means of fermentation, sulfate ions or chloride ions (chlorine ions) have heretofore been generally used as counter anions so as to maintain electrical neutrality of a culture medium. These are supplied mostly in the form of ammonium sulfate as described in, for example, Japanese Patent Application Laid-Open Nos. 30985/'93, 244969/'93, and the like.

Meanwhile, a basic amino acid such as lysine or the like is often sold in the form of the chloride salt (hydrochloride) since it is difficult to crystallize a basic amino acid such lysine or the like in the free state. However, in the production method of a basic amino acid by means of fermentation, since a hydrochloride causes corrosion of a fermentation tank, or the like, a sulfate is often used for fermentation for the purpose of avoiding the corrosion of the tank.

In this case, however, since a basic amino acid product as such resulting from such fermentation is different in counter anion from a basic amino acid product (to be) placed in distribution, the counter anions (such as sulfate ions) are once removed from the basic amino acid salt produced by means of such fermentation, with the use of, e.g., an anion exchange resin and desired counter anions (such as chloride ions) are then added in the form of a free acid, whereby the target basic amino acid salt is produced. Such use of a resin, however, increases loads on environmental protection such as drainage resulting from use of the resin, and the like.

Further, since such use of a resin requires excess acid and alkali, a variety of by-products are also discharged in addition to the target amino acid salt.

In addition, when a basic amino acid such as lysine or the like is to be placed in distribution in the form of a solution-type amino acid feed additive, the solubility of the amino acid in the feed additive solution decreases due to the presence of counter anions, if present therein, so that the counter anions must be removed with the use of a resin in order to obtain an amino acid solution with a high concentration.

In the case of lysine as an example, lysine hydrochloride can be dissolved in water at 10° C. in an amount of at most 43 g in terms of lysine per 100 g of water, and lysine ½ sulfate can be dissolved in an amount of at most 68 g per 100 g of water. On the other hand, in the case of a solution having only lysine dissolved therein (a free lysine solution), the solution is alkaline in nature, and lysine can be dissolved therein in an amount of as much as 120 g per 100 g of water. In this connection, refer to Japanese Patent Application Laid-Open No. 256290/2000.

As could be understood from the above, removal of the counter anions from a basic amino acid solution is essential or indispensable to prepare a basic amino acid solution having a high concentration.

There has been known as a conventional method for purifying an amino acid fermentation broth with the use of an ion exchange membrane, a method (as disclosed in Japanese Patent Publication No. 7666/1960) in which the amino acid moiety in an aqueous solution of an amino acid salt is caused to pass through the ion exchange membranes with the use of an electrodialyser equipped with a plurality of cation exchange membranes and anion exchange membranes, the two kinds of ion exchange membranes being disposed alternately, whereby the amino acid is produced. The performance of the method, however, is not necessarily high in terms of electrical efficiency due to low mobility of organic molecules such amino acid or the like.

Further, in the case of a solution which contains a large amount of various organic metabolites and the like resulting from microbial fermentation, which, in turn, cannot pass through a cation exchange membrane and an anion exchange membrane, their concentrations become so significantly high at the surfaces of the ion exchange membranes that these organic metabolites are deposited or agglomerated and eventually accumulated on the surfaces of the ion exchange membranes to clog the membranes, which ends in making a continuous operation impossible disadvantageously.

SUMMARY OF THE INVENTION

[Problems to be Solved by the Invention]

It is an object of the present invention to provide a method for obtaining a basic amino acid solution having a high concentration within the concentration range in which crystals of a basic amino acid salt are not deposited, by removing the counter anions from a solution of the basic amino acid salt efficiently by use of electrodialysis.

[Means for Solving the Problems]

The present inventors have made extensive and intensive studies to achieve the above object and found that, in removing the counter anions of a basic amino acid by means of electrodialysis, when an alkali aqueous solution is added to a solution of the basic amino acid salt (solution to be subjected to electrodialysis) during the electrodialysis, the counter anions of the basic amino acid such as sulfate ions or the like can be efficiently removed to such degree that they remain in an amount of 40 mol % or smaller based on the amino acid. The present invention has been completed on the basis of these findings.

Accordingly, the present invention relates to a method for producing a basic amino acid solution which comprises subjecting a solution of a basic amino acid salt to electrodialysis with the use of an electrodialyser equipped with cation exchange membranes and anion exchange membranes in combination, wherein an alkali aqueous solution is added to the solution of a basic amino acid salt during the electrodialysis, whereby not only desalting is caused but also the counter anions of the basic amino acid are removed to such degree that the said counter anions remain in an amount of 40 mol % or smaller based on the basic amino acid, and also to a method for producing a basic amino acid solution which comprises subjecting a solution of a basic amino acid salt to electrodialysis with the use of an electrodialyser equipped with anion exchange membrane alone, wherein an alkali aqueous solution is added to the solution of a basic amino acid salt to adjust the pH of the solution to 7 to 10 during the electrodialysis, whereby the counter anions are removed.

DESCRIPTION OF SYMBOLS

Figure 1:
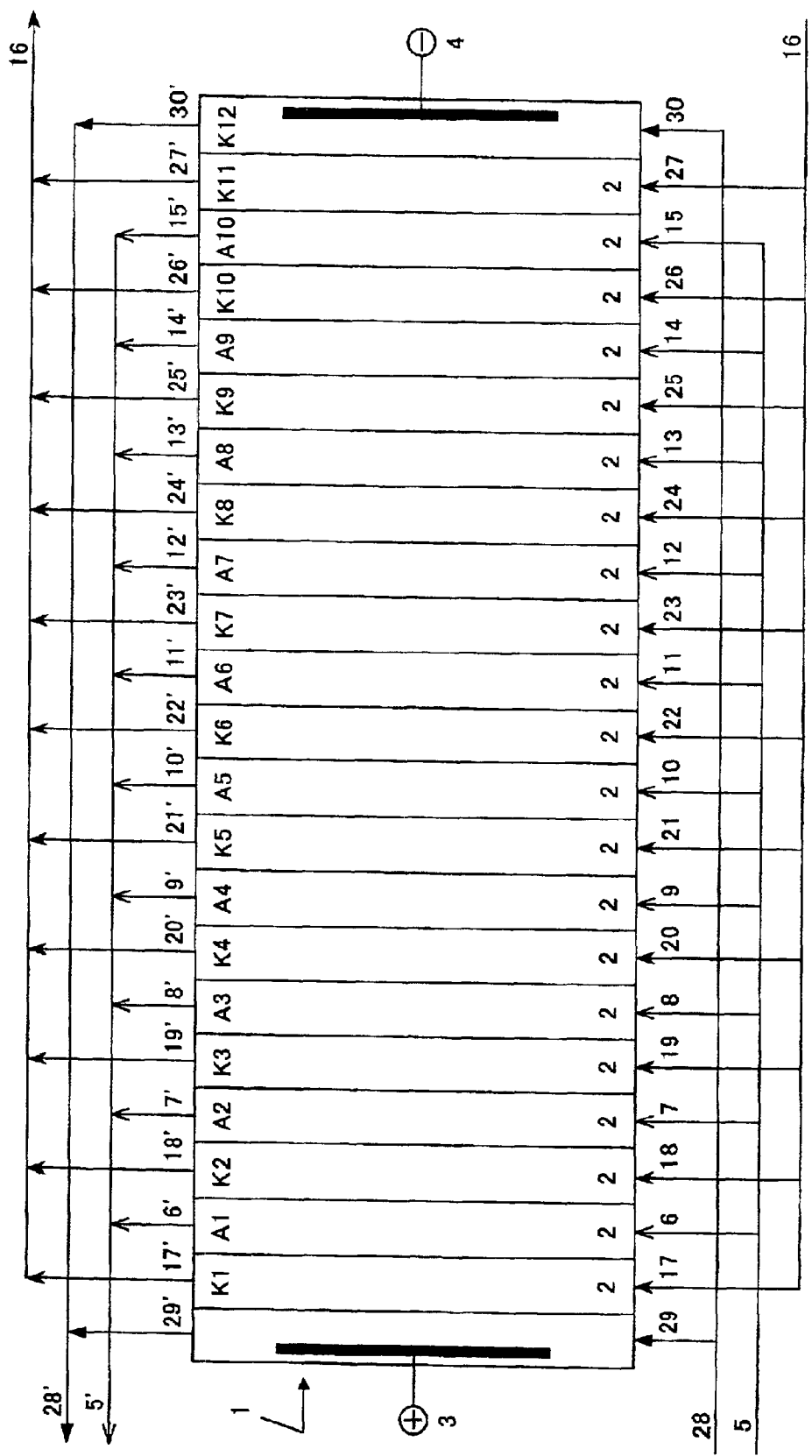
FIG. 1 shows a schematic diagram for illustrating an example of an electrodialyser to be used in the practice of the method of the present invention.

1: ELECTRODIALYSER.
A1 to A10: ANION EXCHANGE MEMBRANES.
K1 to K12: CATION EXCHANGE MEMBRANES.
3: ANODE
4: CATHODE
5 to 15: CONDUITS FOR SUPPLYING A SOLUTION TO BE DIALYZED.
5' to 15': CONDUITS FOR DISCHARGING THE SOLUTION DIALYZED.
16 to 27: CONDUITS FOR SUPPLYING A DIALYSIS SOLVENT FOR COLLECTING THE COUNTER ANIONS DIALYZED.
16' to 27': CONDUITS FOR DISCHARGING THE DIALYSIS SOLVENT WHICH HAS COLLECTED THE DIALYZED COUNTER ANIONS.
28 to 30: CONDUITS FOR SUPPLYING AN ELECTRODE SOLUTION.
28' to 30': CONDUITS FOR DISCHARGING THE ELECTRODE SOLUTION.

DETAILED DESCRIPTION OF THE INVENTION

Hereinbelow, the present invention will be described in great detail.

The method of the present invention is carried out by using an electrodialyser equipped with sulfonic acid type or carboxylic acid type cation exchange membrane(s) and quaternary ammonium base type or tertiary amine type anion exchange membrane(s) in combination or an electrodialyser equipped with quaternary ammonium base type or tertiary amine type anion exchange membrane(s). The number of ion exchange membranes disposed in the electrodialyser, the capacity of the electrodialyser, the number of the isolated chambers for a solution to be dialyzed and for a dialysis solvent in the electrodialyser and the size of the isolated chambers can be selected by those skilled in the art in a given case so appropriately as to achieve the object of the present invention.

There may be mentioned as a specific example of an electrodialyser to be used according to the present invention an electrodialyser in which an anode chamber, a raw material solution chamber (a chamber for a solution to be dialyzed), a salt recovering solvent chamber (dialysis solvent chamber) and a cathode chamber are separated with anion exchange membrane(s) and a cation exchange membrane(s). In the electrodialyser, a 5% sodium sulfate solution or the like is circulated in the cathode and anode chambers. In the raw material solution chamber, a basic amino acid salt solution such as a lysine fermentation broth or the like is made to pass, and in the adjacent salt recovering solvent chamber, pure water or the like is made to pass initially.

A plurality of raw material solution chambers and salt recovering solvent chambers can be of course used. To be more specific, electrodialysis can be carried out with the use of an appratus shown in FIG. 1, for example. In FIG. 1, in an electrodialyser 1, cation exchange membranes K1 K2, K3, . . . , K10 and anion exchange membranes A1, A2, A3, . . . , A10 are disposed alternately, one cation exchange membrane after another anion exchange membrane and cation exchange membranes K11 and K12 are in turn disposed after the anion exchange membrane A10 so as to constitute a plurality of isolated chambers 2, 2, . . . , 2. In the electrodialyser, an anode 3 (anode chamber) and a cathode 4 (cathode chamber) are provided at the ends so as to oppose each other.

A sample solution (raw material solution, solution to be dialyzed) is supplied into the electrodialyser via a conduit 5 and branch pipes 6, 7, 8, . . . , 15, flows through raw material solution chambers between the anion exchange membranes and the cation exchange membranes, and is discharged from the electrodialyser via branch pipes 6', 7', 8', . . . , 15' and a conduit 5'. Further, a dialysis solvent such as pure water or the like for collecting the dialyzed counter anions is supplied into the electrodialyser via a conduit 16 and branch pipes 17, 18, 19, . . . , 27 and discharged from the electrodialyser via branch pipes 17', 18', 19', . . . , 27' and a conduit 16'. Meanwhile, a solution of a salt such as sodium sulfate which is appropriate as an electrode is introduced into the electrodialyser via a conduit 28 and branch pipes 29 and 30 and discharged from the electrodialyser via branch pipes 29' and 30' and a conduit 28'. During this operation, a direct current is made to pass between the electrodes.

According to the above-described electrodialysis using cation exchange membranes and anion exchange membranes in combination, desalting is carried out in addition to removal of counter anions. The removal of counter anions can still be achieved with the sole use of anion exchange membranes, in addition to the above concurrent use of cation exchange membranes and anion exchange membranes.

When only anion exchange membranes are used, an electrodialyser obtained by replacing all the cation exchange membranes K1, K2, K3, . . . , K10 of the electrodialyser shown in FIG. 1 with anion exchange membranes can be used, for example. As a dialysis solvent to be supplied into the electrodialyser via the conduit 16 and the branch pipes 17, 18, 19, . . . , 27 and discharged from the electrodialyser via the branch pipes 17', 18', 19', . . . , 27' and the conduit 16', an alkal aqueous solution can be used. A solution to be dialyzed is subjected to electrodialysis after an alkali aqueous solution is added to the solution to adjust the pH of the solution to 7 to 10 so as to remove counter anions.

As an inflow velocity of the sample solution, a membrane surface linear velocity of not lower than 1 cm/sec, preferably 4 to 6 cm/sec, can be used. Conditions for electrodialysis such as a current density, a voltage, a duration of electrodialysis, and the like can be selected appropriately, depending upon characteristics of a basic amino acid salt solution which is a solution to be dialyzed, coexisting salts, the types and numbers of cation exchange membranes and anion exchange membranes to be used, the size of an electrodialyser, and the like. In general, good results can be obtained at a current density of about 1 to 5 A/dm$^2$. The temperature can be room temperature to 70° C.

When electrodialysis is carried out by concurrent use of cation exchange membranes and anion exchange membranes, counter anions are dialyzed via the anion exchange membranes and removed from the raw material solution chambers, while foreign cations are dialyzed via the cation exchange membranes and removed into the salt recovering chambers. In this case, in order to remove the counter anions of a basic amino acid with the basic amino acid being left in the raw material solution, the amount of cations to be removed into the salt recovering chambers gets relatively insufficient. Therefore, an alkali aqueous solution such as ammonia water or the like which contains cations which pass through the cation exchange membranes easily, is added to the raw material solution, whereby the counter anions of the basic amino acid can be removed into the salt recovering solvent without the target amino acid being lost into the salt recovering solvent.

Illustrative examples of anion exchange membranes and cation exchange membranes to be used according to the production method of the present invention include "CEMI-LEON AMV" and "CELEMION CMV" (products of Asahi Glass Company), and "ACIPLEX A-211" and "ACIPLEX A-201", and "ACIPLEX K-101" (products of Asahi Kasei Corporation).

As ion exchange membranes to be used for electrodialysis according to present invention, ordinary ion exchange membranes as described above may be used. However, the fractional molecular weight of a cation exchange membrane is preferably smaller than the molecular weight of the basic amino acid from the viewpoint of prevention of outflow of the basic amino acid and, for example, a cation exchange membrane having a fractional molecular weight of about 100 is preferably used. On the other hand, when the fractional molecular weight of an anion exchange membrane is too small, efficiency of removal of counter anions is reduced. Therefore, a membrane having a fractional molecular weight slightly larger than the molecular weight of the main anions to be removed, is preferably used. E.g., when sulfate ions are to be removed, they can be removed efficiently with the use of a membrane having a fractional molecular weight of at least 300, for example.

An alkali aqueous solution to be added and used according the production method of the present invention is not particularly limited, and may be ammonia water or an aqueous solution of a hydroxide of an alkali metal such as sodium, potassium or the like, for example. However, when a desalted solution resulting from electrodialysis is to be concentrated, use of ammonia water makes it possible to remove ammonia into the drain. Therefore, in this case, use of ammonia is preferred. However, it is not limited thereto when the concentration is carried out by loose RO or the like.

The concentration of the alkali aqueous solution is not particularly limited, either. However, when the solution gets diluted, loads on concentration or the like in the subsequent step increase. To avoid this, the concentration of ammonia water should be 25 to 29%, and the concentration of an alkali aqueous solution containing cations of an alkali metal such as sodium or the like should be around 25 to 48%.

The amount of an alkali to be added and used is such an amount that is an equimolar amount of the anions to be removed or an amount corresponding to electric charges of the basic amino acid as required, in addition thereto. An excess amount of an alkali exceeding the amount is not necessary.

As an amino acid solution to be subjected to electrodialysis according to the present invention, a basic amino acid solution having a basic amino acid salt such as commercially available lysine hydrochloride or the like dissolved therein, can be used. In addition, an amino acid solution obtained by a synthesis method, a fermentation method, a proteolysis method or the like, as well as a crystallization mother liquor resulting from crystallization of crystals of lysine hydrochloride or the like, can also be used.

Further, in the basic amino acid salt solution to be subjected to electrodialysis, cations, proteins, organic acids or the like derived from a fermentation broth or a synthesis solution may be contained in such amounts that do not inhibit the efficiency of the electrodialysis.

Regarding addition of an alkali aqueous solution at the time of electrodialysis, it may be added to a basic amino acid salt solution to be subjected to electrodialysis in advance or may be added gradually during the electrodialysis process.

A basic amino acid solution produced by the production method of the present invention and having a reduced amount of counter ions can be concentrated to a high concentration because an amino acid is not easily deposited therefrom when concentrated. Although such a high-concentration amino acid solution can be used as it is as an amino acid solution, it can be highly purified by adding desired counter anions such as chloride ions or the like in the form of an free acid, whereby crystals of a basic amino acid salt are formed.

Further, utilization of the present invention makes it possible to convert a basic amino acid solution having a variety of counter anions into an amino acid salt having a desired kind of counter anions.

A salt waste solvent (salt-recovered solvent) obtained by use of the present invention contains salts derived mainly from the counter anions. Therefore, the salts can be recovered from the salt waste solvent and recycled as raw materials for fermentation or the like.

EXAMPLES

The present invention will be described in detail with reference to examples hereinafter.

Example 1

Concurrent Use of Cation Exchange Membranes and Anion Exchange Membranes (Fermentation Broth)

Electrodialysis was carried out by use of 1,040 g of a lysine solution obtained by removing the microbial cells by means of an ultrafiltration membrane from a lysine fermentation broth obtained by culturing a microorganism having a lysine producing capability. The concentration of lysine in the solution to be subjected to electrodialysis was 9.7%, and the concentration of sulfate ions as the counter anions was 4.0%. In addition to these, 0.3% of organic acids and 0.25% of alkali metal ions such as potassium ions, sodium ions and the like were also contained therein. This solution was subjected to electrodialysis with the use of a "Micro Acilyzer G3" electrodialyser of Asahi Kasei corporation. The ion exchange membrane used in the electrodialysis was an "AC-120–400 type" membrane comprising cation exchange membranes and anion exchange membranes in combination. The fractional molecular weight of the cation exchange membranes was 100, and the fractional molecular weight of the anion exchange membranes was 300, the membrane areas of the cation and anion exchange membranes being both 400 $cm^2$.

The electrodialysis was initiated by use of 300 g of pure water as the dialysis solvent as a salt recovering solvent. After 8 minutes from the initiation of the electrodialysis, addition of 28% ammonia water was started to the solution to be dialyzed at a rate of 0.8 g/min, and the electrodialysis was then continued until no reduction in conductivity was recognized. The average electric current and the average voltage during the electrodialysis were 1.4 $A/dm^2$ and 13.8 V, respectively. The time spent for the electrodialysis was 120 minutes, and the final pH of the solution dialyzed was 9.6.

When the amino acid solution after the electrodialysis was analyzed, 94% of the lysine had been recovered. At this point in time, 75% of the sulfate ions which were the counter anions had been removed, and the proportion thereof was reduced to 33 mol % based on the lysine. The removal ratio of the alkali metal ions such as potassium ions, sodium ions and the like was 90%, and the removal ratio of the ammonium ions including the added portion was 80%. The removal ratio of the organic acids was 45%, and the amount of the lysine in the solid content of the solution was increased to 85% from 65% as compared with that before the electrodialysis (increase in purity). This solution was concentrated by removing the ammonia therefrom, whereby a high-concentration lysine solution having a concentration of 51% could be prepared at room temperature without observing deposition of lysine crystals.

Example 2

Concurrent Use of Cation Exchange Membranes and Anion Exchange Membranes (Fermentation Broth)

Electrodialysis was carried out by use of 998 g of a lysine solution obtained by removing the microbial cells by means of an ultrafiltration membrane from a lysine fermentation broth obtained by culturing a microorganism having a lysine producing capability. The concentration of lysine in the solution to be subjected to electrodialysis was 12%, the concentration of sulfate ions as the counter anions was 1.3%, and the concentration of chloride ions (chlorine ions) was 2.4%. In addition to these, 0.3% of alkali metal ions such as potassium ions, sodium ions and the like was also contained therein. This solution was subjected to electrodialysis with the use of a "Micro Acilyzer G3" electrodialyser of Asahi Kasei Corporation. The ion exchange membrane used in the electrodialysis was an "AC-120–400 type" membrane comprising cation exchange membranes and anion exchange membranes in combination. The fractional molecular weight of the cation exchange membranes was 100, and the fractional molecular weight of the anion exchange membranes was 300, the membrane areas of the cation and anion exchange membranes being both 400 $cm^2$.

The electrodialysis was initiated by use of 300 g of pure water as the dialysis solvent as a salt recovering solvent. After 5 minutes from the initiation of the electrodialysis, addition of 28% ammonia water was started to the solution to be dialyzed at a rate of 0.72 g/min, and the electrodialysis was then continued until no reduction in conductivity was recognized. The time spent for the electrodialysis was 100 minutes, and the final pH of the solution dialyzed was 9.3.

When the amino acid solution after the electrodialysis was analyzed, 94% of the lysine had been recovered. At this point in time, 97% of the chloride ions had been removed, 80% of the sulfate ions had been removed, and the remaining counter anions had been reduced to 29 mol % based on the lysine. The removal ratio of the alkali metal ions such as potassium ions, sodium ions and the like was 90%, and the amount of the lysine in the solid content of the solution was increased to 82% from 65% as compared with that before the electrodialysis (increase in purity). This solution was concentrated by removing the ammonia therefrom, whereby a high-concentration lysine solution having a concentration of 49% could be prepared at room temperature without observing deposition of lysine crystals.

Example 3

Concurrent Use of Cation Exchange Membranes and Anion Exchange Membranes (Crystallization Mother Liquor)

Electrodialysis was carried out by use of a solution obtained by adding 300 g of pure water to 470 g of a crystallization mother liquor resulting from removal of the lysine hydrochloride crystals from a lysine solution obtained by removing the microbial cells by means of an ultrafiltration membrane from a lysine fermentation broth obtained by culturing a microorganism having a lysine producing capability. The concentration of lysine in the solution to be subjected to electrodialysis was 10.9%, the concentration of chloride ions was 4.25%, the concentration of sulfate ions was 5.7%, the concentration of sodium ions was 0.6%, the concentration of potassium ions was 0.55%, the concentration of ammonium ions was 1.9%, and the concentration of organic acids was 1.3%. The proportion of lysine in the solid content of this solution was 34%. This solution was subjected to electrodialysis by use of a "Micro Acilyzer G3" electrodialyser of Asahi Kasei Corporation. The ion exchange membrane used in the electrodialysis was an "AC-120–400 type" membrane, the fractional molecular weight of the cation exchange membranes was 100, and the fractional molecular weight of the anion exchange membranes was 300, the membrane areas of the cation and anion exchange membranes being both 400 $cm^2$.

The electrodialysis was initiated by use of 300 g of pure water as the dialysis solvent as a salt recovering solvent. After 70 minutes from the initiation of the electrodialysis where the voltage which had been once decreased began to be increased again, addition of 28% ammonia water was started to the solution to be dialyzed at a rate of 0.64 g/min, and the electrodialysis was continued until no reduction in conductivity was recognized after the electric current was decreased. The time spent for the electrodialysis was 150 minutes, and the final pH of the solution dialyzed was 9.4. The average electric current and the average voltage during the electrodialysis were 2 $A/dm^2$ and 12.2 V, respectively.

When the amino acid solution after the electrodialysis was analyzed, 94.5% of the lysine had been recovered. At this point in time, 96% of the chloride ions had been removed, 90% of the sulfate ions had been removed, and the proportion of the remaining counter anions was reduced to 21 mol % based on the lysine. The removal ratio of the alkali metal ions such as potassium ions, sodium ions and the like was 96%, and the removal ratio of the ammonium ions including the added portion was 85%. The removal ratio of the organic acids was 57% on the average, and the amount of the lysine in the solid content of the solution was increased to 53% from 34% as compared with that before the electrodialysis (increase in purity). This solution was concentrated by removing the ammonia therefrom, whereby a high-concentration lysine solution having a concentration of 32% could be prepared without observing deposition of lysine crystals, though it was increased in viscosity to 2.4 Pa·s($10°$ C.), said concentration of 32% being about three times 10.9% which was, in turn, the lysine concentration of the crystallization mother liquor before the electrodialysis.

Example 4

Concurrent Use of Cation Exchange Membranes and Anion Exchange Membranes (Crystallization Mother Liquor)

Electrodialysis was carried out by use of a solution obtained by adding 300 g of pure water to 467 g of a crystallization mother liquor resulting from removal of the lysine hydrochloride crystals from a lysine solution obtained by removing the microbial cells by means of an ultrafiltration membrane from a lysine fermentation broth obtained by culturing a microorganism having a lysine producing capability. The concentration of lysine in the solution to be subjected to electrodialysis was 10.8%, the concentration of chloride ions was 4.05%, the concentration of sulfate ions was 5.3%, the concentration of sodium ions was 0.5%, the concentration of potassium ions was 0.5%, the concentration of ammonium ions was 1.8%, and the concentration of organic acids was 1.3%. The proportion of lysine in the solid content of this solution was 34%. This solution was subjected to electrodialysis by use of a "Micro Acilyzer G3" electrodialyser of Asahi Kasei Corporation. The ion exchange membrane used in the electrodialysis was an "AC-130–400 type" membrane, the fractional molecular weight of the cation exchange membranes was 100, and the fractional molecular weight of the anion exchange membranes was 300, the membrane areas of the cation and anion exchange membranes being both 400 $cm^2$.

The electrodialysis was initiated by use of 300 g of pure water as the dialysis solvent as a salt recovering solvent. After 80 minutes from the initiation of the electrodialysis where the voltage which had been once decreased began to be increased again, addition of 28% ammonia water was started to the solution to be dialyzed at a rate of 0.61 g/min, and the electrodialysis was continued until no reduction in conductivity was recognized after the electric current was decreased. The time spent for the electrodialysis was 180 minutes, and the final pH of the solution dialyzed was 9.6. The average electric current and the average voltage during the electrodialysis were 1.9 $A/dm^2$ and 11.2 V, respectively.

When the amino acid solution after the electrodialysis was analyzed, 90% of the lysine had been recovered. At this point in time, 95% of the chloride ions had been removed, 80% of the sulfate ions had been removed, and the proportion of the remaining counter anions was reduced to 39 mol % based on the lysine. The removal ratio of the alkali metal ions such as potassium ions, sodium ions and the like was 96%, and the removal ratio of the ammonium ions including the added portion was 85%. The removal ratio of the organic acids was 67% on the average, and the amount of the lysine in the solid content of the solution was increased to 50% from 34% as compared with that before the electrodialysis (increase in purity). This solution was concentrated by removing the ammonia therefrom, whereby a high-concentration lysine solution having a concentration of 31% could be prepared without observing deposition of lysine crystals, said concentration of 31% being about three times 10.8% which was, in turn, the lysine concentration of the crystallization mother liquor before the electrodialysis.

Example 5

Concurrent Use of Cation Exchange Membranes and Anion Exchange Membranes (Crystallization Mother Liquor)

Electrodialysis was carried out by use of a solution obtained by adding 300 g of pure water to 470 g of a crystallization mother liquor resulting from removal of the lysine hydrochloride crystals from a lysine solution obtained by removing the microbial cells by means of an ultrafiltration membrane from a lysine fermentation broth obtained by culturing a microorganism having a lysine producing capability. The concentration of lysine in the solution to be subjected to electrodialysis was 9.9%, the concentration of chloride ions was 4.1%, the concentration of sulfate ions was 5.7%, the concentration of sodium ions was 0.6%, the concentration of potassium ions was 0.56%, the concentration of ammonium ions was 1.8%, and the concentration of organic acids was 1.3%. The proportion of lysine in the solid content of this solution was 34%. This solution was subjected to electrodialysis by use of a "Micro Acilyzer G3" electrodialyser of Asahi Kasei Corporation. The ion exchange membrane used in the electrodialysis was an "AC-120–400 type" membrane, the fractional molecular weight of the cation exchange membranes was 100, and the fractional molecular weight of the anion exchange membranes was 300, the membrane areas of the cation and anion exchange membranes being both 400 $cm^2$.

The electrodialysis was initiated by use of 300 g of pure water as the dialysis solvent as a salt recovering solvent. After 84 minutes from the initiation of the electrodialysis where the voltage which had been once decreased began to be increased again, addition of 28% ammonia water was carried out in an amount of 99.6 g until the pH of the solution to be dialyzed got to the isoelectyric point of lysine, and the electrodialysis was continued until no reduction in conductivity was recognized after the electric current was decreased. The time spent for the electrodialysis was 208 minutes.

When the amino acid solution after the electrodialysis was analyzed, 75% of the lysine had been recovered. At this point in time, 98% of the chloride ions had been removed, 94% of the sulfate ions had been removed, and the proportion of the remaining counter anions was reduced to 19 mol % based on the lysine. The removal ratio of the alkali metal ions such as potassium ions, sodium ions and the like was 95%, and the removal ratio of the ammonium ions including the added portion was 93%. The removal ratio of the organic acids was 67% on the average, and the amount of the lysine in the solid content of the solution was increased to 50% from 34% as compared with that before the electrodialysis (increase in purity). This solution was concentrated by removing the ammonia therefrom, whereby a high-concentration lysine solution having a concentration of 30% could be prepared without observing deposition of lysine crystals, said concentration of 30% being about three times 9.9% which was, in turn, the lysine concentration of the crystallization mother liquor before the electrodialysis.

Example 6

Sole Use of Anion Exchange Membranes

Electrodialysis was carried out by use of 8,560 g of a lysine solution obtained by removing the microbial cells by means of an ultrafiltration membrane from a lysine fermentation broth obtained by culturing a microorganism having a lysine producing capability. The concentration of lysine in a solution to be subjected to electrodialysis was 10.0%, the concentration of sulfate ions as the counter anions was 3.8%, the concentration of organic acids was 0.3%, and the concentration of alkali metal ions such as potassium ions, sodium ions and the like was 0.25%. As an electrodialyser, a commercially available experimental electrodialyser "CELEMION ELECTODIALYSER DU-06" of Asahi Kasei Corporation was used. Twenty sheets of commercially available anion exchange membrane "CELEMION AMV" of Asahi Glass Corporation were installed in the electrodialyser with an effective area of 209 $cm^2$/sheet at an interval between the sheets of 2 mm. An alkali solution was passed through the anode chamber, a lysine solution which was a solution to be dialyzed was passed through a chamber adjacent to the anode chamber, and an alkali aqueous solution as the dialysis solvent was passed through a chamber adjacent to the chamber through which the lysine solution was passed, and so on, whereby the lysine solution to be dialyzed and the alkali aqueous solution as the dialysis solvent were passed alternately, through next chamber to each other, and concurrently. In the last cathode chamber, a sodium hydroxide aqueous solution was circulated in such a manner that it was isolated from other alkali aqueous solutions.

The electrodialysis was continued by passing a current of 1 A/dm$^2$ through the electrodialyser while a solution obtained by adjusting the pH of the lysine solution which was a solution to be dialyzed to a pH of 8.5 by use of ammonia solution was circulated at a rate of 35 L/hr on the average. As a result, it took 4 hours and 30 minutes to complete removal of the anions.

When the amino acid solution after the electrodialysis was analyzed, 96% of the lysine had been recovered. At this point in time, 72% of the sulfate ions which were the counter anions had been removed, and the proportion thereof was reduced to 33 mol % based on the lysine. The amount of the lysine in the solid content of the solution was increased to 83% from 65% as compared with that before the electrodialysis (increase in purity). This solution was concentrated by removing the ammonia therefrom, whereby a high-concentration lysine solution having a concentration of 48% could be prepared at room temperature without observing deposition of lysine crystals.

Comparative Example 1

Non-Addition of Alkali Aqueous Solution

Electrodialysis was carried out by use of a solution obtained by adding 300 g of pure water to 474 g of a crystallization mother liquor resulting from removal of the lysine hydrochloride crystals from a lysine solution obtained by removing the microbial cells by means of an ultrafiltration membrane from a lysine fermentation broth obtained by culturing a microorganism having a lysine producing capability. The concentration of lysine in the solution to be subjected to electrodialysis was 10.8%, the concentration of chloride ions was 3.9%, the concentration of sulfate ions was 4.9%, the concentration of sodium ions was 0.41%, the concentration of potassium ions was 0.39%, the concentration of ammonium ions was 1.8%, and the concentration of organic acids was 1.0%. The proportion of lysine in the solid content of this solution was 34%. This solution was subjected to electrodialysis by use of a "Micro Acilyzer G3" electrodialyser of Asahi Kasei Corporation. The ion exchange membrane used in the electrodialysis was an "AC-120–400 type" membrane, the fractional molecular weight of the cation exchange membranes was 100, and the fractional molecular weight of the anion exchange membranes was 300, the membrane areas of the cation and anion exchange membranes being both 400 cm$^2$.

The electrodialysis was initiated by use of 300 g of pure water as the dialysis solvent as a salt recovering solvent. After the initiation of the electrodialysis, the voltage was once decreased and increased again, and the electric current began to be decreased. The electrodialysis was continued until no reduction in conductivity was recognized after the electric current was decreased enough. The time spent for the electrodialysis was 150 minutes, and the pH of the solution dialyzed was 5.9.

When the amino acid solution after the electrodialysis was analyzed, 92% of the lysine had been recovered, and 92% of the chloride ions had been removed. However, only 50% of the sulfate ions had been removed, and the proportion of the remaining counter anions was 130 mol % based on the lysine.

It can be understood from the above that although removal of excess salts might be achieved by mere electrodialysis, it fails to remove the counter anions of lysine. Further, the amount of lysine in the solid content of the solution was increased to at most 45% from 34%, and an increase in purity was small as compared with Example 3.

[Effect of the Invention]

As described above, according to the present invention, the counter anions as well as excess salts can be removed from a solution of the salt of a basic amino acid such as lysine or the like, by adding an alkali aqueous solution such as ammonia water or the like to the solution when subjected to electrodialysis. Thereby, a high-concentration amino acid solution can be produced, and costs in transportation and preservation of a basic amino acid can be reduced. Further, when a basic amino acid solution is subjected to spray granulation or the like, a solution having a high concentration can be subjected to spraying. In addition, since counter anions can be removed from a fermentation broth or the like of a basic amino acid salt or the like according to the present invention, crystals of an amino acid salt having the target counter anions can be produced by adding the desired anions to the solution again.

What is claimed is:

1. A method for producing a basic amino acid solution which comprises:
   a) subjecting the solution comprising a basic amino acid salt to electrodialysis in an electrodialyser equipped with one or more cation exchange membranes and one or more anion exchange membranes in combination for a time sufficient for the voltage across the electrodialysis to begin increasing subsequent to a initial voltage decrease;
   b) adding an alkali aqueous solution to the solution comprising a basic amino acid salt in an amount sufficient to increase the pH to a value ranging from 7 to 10;
   c) subjecting the solution of (b) to electrodialysis until no further reduction in conductivity is observed; and
   d) recovering a solution containing an enriched population of the basic amino acid.

2. The method of claim 1, wherein said cation exchange membrane is selected from the group consisting of a sulfonic acid-type cation exchange membrane and a carboxylic acid-type cation exchange membrane.

3. The method of claim 1, wherein said anion exchange membrane is selected from the group consisting of a quaternary ammonium base-type anion exchange membrane and a tertiary amine-type anion exchange membrane.

4. The method of claim 1, wherein said basic amino is selected from the group consisting of lysine, arginine, and histidine.

5. The method of claim 1, wherein the electrodialyser comprise an anode chamber, one or more raw material solution chambers, one or more salt recovering solvent chambers, and a cathode chamber, wherein the chambers are separated with one or more anion exchange membranes and one or more cation exchange membranes.

6. The method of claim 5, wherein said cation exchange membrane is selected from the group consisting of a sulfonic acid-type cation exchange membrane and a carboxylic acid-type cation exchange membrane.

7. The method of claim 5, wherein said anion exchange membrane is selected from the group consisting of a quaternary ammonium base-type anion exchange membrane and a tertiary amine-type anion exchange membrane.

8. The method of claim 5, wherein a 5% sodium sulfate solution is circulated in the anode chamber and the cathode chamber.

9. The method of claim 5, wherein the fractional molecular weight of a cation exchange membrane is smaller than the molecular weight of the basic amino acid.

10. The method of claim 5, wherein the fractional molecular weight of an anion exchange membrane is larger than the molecular weight of the anions to be removed.

11. The method of claim 5, wherein the alkali aqueous solution is ammonia water.

12. The method of claim 11, wherein the concentration of the ammonia water ranges from 25 to 29%.

13. The method of claim 5, wherein the alkali aqueous solution is an aqueous solution of a hydroxide of an alkali metal.

14. The method of claim 13, wherein the concentration of the aqueous solution of a hydroxide of an alkali metal ranges from 25 to 48%.

15. The method of claim 13, wherein the alkali metal is sodium or potassium.

16. The method of claim 5, wherein said solution comprising a basic amino acid salt is a commercially available lysine hydrochloride solution.

17. The method of claim 5, wherein said solution comprising a basic amino acid salt is obtained by a method selected from the group consisting of a synthesis method, a fermentation method, and a proteolysis method.

18. The method of claim 5, wherein said solution comprising a basic amino acid salt is a crystallization mother liquor obtained by crystallization of crystals of lysine hydrochloride.

19. The method of claim 5, wherein said basic amino acid is selected from the group consisting of lysine, arginine, and histidine.

\* \* \* \* \*

UNITED STATES PATENT AND TRADEMARK OFFICE
CERTIFICATE OF CORRECTION

PATENT NO. : 6,800,185 B2
DATED : October 5, 2004
INVENTOR(S) : Kazuhiro Hasegawa et al.

It is certified that error appears in the above-identified patent and that said Letters Patent is hereby corrected as shown below:

Column 6,
Line 9, "utiligation" should read -- utilization --

Column 12,
Line 43, "amino is" should read -- amino acid is --
Line 46, "comprise" should read -- comprises --

Signed and Sealed this

Nineteenth Day of April, 2005

JON W. DUDAS
*Director of the United States Patent and Trademark Office*